United States Patent
Martin

(10) Patent No.: US 9,708,345 B1
(45) Date of Patent: Jul. 18, 2017

(54) AMINOTHIAZINE COMPOUNDS

(71) Applicant: Eli Lilly and Company, Indianapolis, IN (US)

(72) Inventor: Fionna Mitchell Martin, Berkshire (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/115,280

(22) PCT Filed: Mar. 5, 2015

(86) PCT No.: PCT/US2015/018909
§ 371 (c)(1),
(2) Date: Jul. 29, 2016

(87) PCT Pub. No.: WO2015/138208
PCT Pub. Date: Sep. 17, 2015

Related U.S. Application Data

(60) Provisional application No. 61/953,206, filed on Mar. 14, 2014.

(51) Int. Cl.
*C07D 513/04* (2006.01)
(52) U.S. Cl.
CPC .................. *C07D 513/04* (2013.01)

(58) Field of Classification Search
CPC .................................................... C07D 513/04
USPC ......................................... 514/224.2; 544/48
See application file for complete search history.

(56) References Cited

U.S. PATENT DOCUMENTS

| | | | |
|---|---|---|---|
| 8,158,620 B2 | 4/2012 | Suzuki et al. | |
| 8,629,270 B2 | 1/2014 | Lopez et al. | |
| 8,841,293 B1 | 9/2014 | Green et al. | |
| 9,328,124 B2 * | 5/2016 | Martin | A61K 45/06 |
| 2009/0209755 A1 | 8/2009 | Suzuki et al. | |
| 2013/0261111 A1 | 10/2013 | Beck et al. | |

FOREIGN PATENT DOCUMENTS

WO 2014/013076 1/2014

OTHER PUBLICATIONS

International Search Report and Written Opinion of the International Searching Authority for X20057.

* cited by examiner

*Primary Examiner* — Kahsay Habte
(74) *Attorney, Agent, or Firm* — Nelsen L. Lentz

(57) ABSTRACT

The present invention provides a compound of Formula (I); or a pharmaceutically acceptable salt thereof.

7 Claims, No Drawings

AMINOTHIAZINE COMPOUNDS

The present invention relates to novel aminothiazine compounds, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease.

WO 2014/013076 discloses isothiourea derivatives which are BACE inhibitors useful for treating neurodegenerative diseases caused by Abeta peptide, such as Alzheimer's-type dementia. U.S. Pat. No. 8,158,620 discloses fused amino-dihydrothiazine derivatives which possess BACE inhibitory activity, and are further disclosed as useful therapeutic agents for a neurodegenerative disease caused by Abeta peptide, such as Alzheimer's type dementia.

BACE inhibitors with central nervous system (CNS) penetration are desired to provide treatments for Abeta peptide-mediated disorders, such as Alzheimer's disease. The present invention provides certain novel compounds that are inhibitors of BACE. In addition, the present invention provides certain novel compounds which penetrate the CNS, have an improved side effect profile, and improved physicochemical properties, such as improved solubility.

Accordingly, the present invention provides a compound of Formula I:

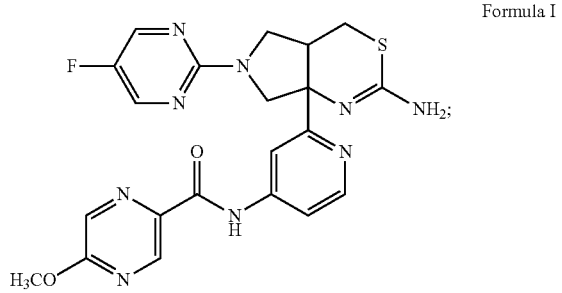 [SMILES: COc1cnc(C(=O)Nc2ccnc(C34CN(c5ncc(F)cn5)CC3CSC(N)=N4)c2)cn1]

Formula I or a pharmaceutically acceptable salt thereof.

The present invention also provides a method of treating Alzheimer's disease, comprising administering to a patient in need of such treatment an effective amount of a compound of Formula I, or a pharmaceutically acceptable salt thereof.

The present invention further provides a method of preventing the progression of mild cognitive impairment to Alzheimer's disease in a patient, comprising administering to a patient in need of such treatment an effective amount of a compound of Formula I, or a pharmaceutically acceptable salt thereof.

The present invention also provides a method of inhibiting BACE in a patient, comprising administering to a patient in need of such treatment an effective amount of a compound of Formula I, or a pharmaceutically acceptable salt thereof.

The present invention also provides a method for inhibiting BACE-mediated cleavage of amyloid precursor protein, comprising administering to a patient in need of such treatment an effective amount of a compound of Formula I, or a pharmaceutically acceptable salt thereof.

The invention further provides a method for the inhibition of production of Abeta peptide, comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy. In addition, this invention provides a compound of Formula I or a pharmaceutically acceptable salt thereof for use in the treatment of Alzheimer's disease. This invention provides a compound of Formula I or a pharmaceutically acceptable salt thereof for use in the prevention of the progression of mild cognitive impairment to Alzheimer's disease. Even furthermore, this invention provides the use of a compound of Formula I, or a pharmaceutically acceptable salt thereof, for the manufacture of a medicament for the treatment of Alzheimer's disease. This invention also provides the use of a compound of Formula I, or a pharmaceutically acceptable salt thereof, for the manufacture of a medicament for the prevention of the progression of mild cognitive impairment to Alzheimer's disease.

The invention further provides a pharmaceutical composition, comprising a compound of Formula I, or a pharmaceutically acceptable salt thereof, with one or more pharmaceutically acceptable carriers, diluents, or excipients. In a particular embodiment, the composition further comprises one or more other therapeutic agents. This invention also encompasses novel intermediates and processes for the synthesis of the compounds of Formula I.

The term "prevention of the progression of mild cognitive impairment to Alzheimer's disease" includes slowing, arresting, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formula I are particularly useful in the treatment methods of the invention, but certain groups, substituents, and configurations are preferred for compounds of Formula I. The following paragraphs describe such preferred groups, substituents, and configurations. It will be understood that these preferences are applicable both to the treatment methods and to the new compounds of the invention.

The compound of the following formula in the cis configuration:

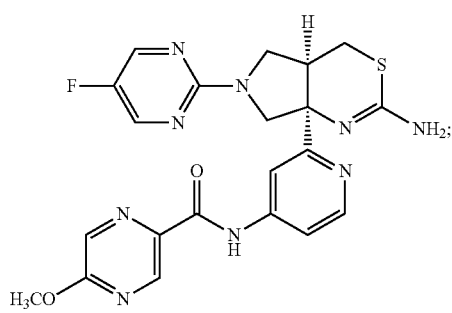 [SMILES: COc1cnc(C(=O)Nc2ccnc([C@]34CN(c5ncc(F)cn5)C[C@H]3CSC(N)=N4)c2)cn1]

or a pharmaceutically acceptable salt thereof is preferred.

N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide or a pharmaceutically acceptable salt thereof is further preferred.

N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide is especially preferred.

One of ordinary skill in the art will appreciate that compounds of the invention are comprised of a core that contains two chiral centers as shown below in Scheme A:

Scheme A

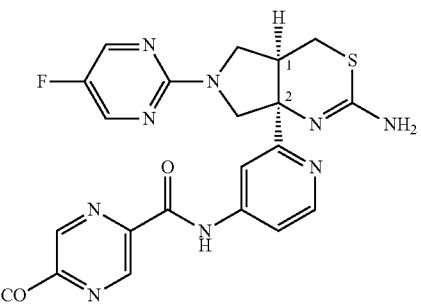

Although the present invention contemplates all individual enantiomers and diasteromers, as well as mixtures of the enantiomers of said compounds, including racemates, the compounds with the absolute configuration at the carbon atoms labeled 1 and 2 as illustrated in Scheme A are preferred compounds of the invention.

One of ordinary skill in the art will appreciate that compounds of the invention can exist in tautomeric forms, as depicted in Scheme B. When any reference in this application to one of the specific tautomers of the compounds of the invention is given, it is understood to encompass both tautomeric forms and all mixtures thereof.

Scheme B

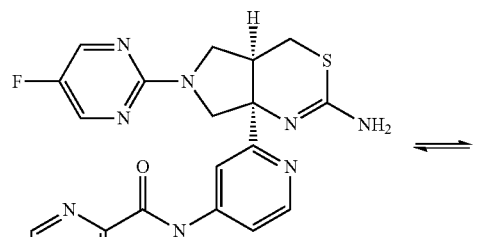

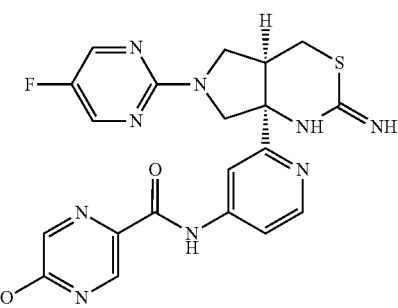

Certain stereochemical centers have been left unspecified for the sake of clarity and are not intended to limit the teaching of the preparations and examples in any way. Furthermore, individual isomers, enantiomers, and diastereomers may be separated or resolved by one of ordinary skill in the art at any convenient point in the synthesis of compounds of Formula I by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

Additionally, certain intermediates described in the following preparations may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "APP" refers to amyloid precursor protein; "DMEM" refers to Dulbecco's Modified Eagle's Medium; "DMSO" refers to dimethyl sulfoxide; "F12" refers to Ham's F12 medium; "FBS" refers to Fetal Bovine Serum; "FRET" refers to fluorescence resonance energy transfer; "HB-PS" refers to HEPES-buffered physiological saline; "HEK" refers to human embryonic kidney; "HEPES" refers to 2[4-(2-hydroxyethyl)piperazin-1-yl]ethanesulfonic acid; "HPLC" refers to high-performance liquid chromatography; "$IC_{50}$" refers to the concentration of an agent that produces 50% of the maximal inhibitory response possible for that agent; "JohnPhos" refers to ditert-butyl-(2-phenylphenyl)phosphane; "min" refers to minute or minutes; "MTBE" refers to methyl tert-butyl ether; "PDAPP" refers to platelet derived amyloid precursor protein; "RFU" refers to relative fluorescence unit; "SFC" refers to supercritical fluid chromatography; and "SEM" refers to standard error of the mean.

The compounds of the present invention, or salts thereof, may be prepared by a variety of procedures known in the art, some of which are illustrated in the Preparations and Examples below. The specific synthetic steps for each of the routes described may be combined in different ways to prepare compounds of Formula I, or salts thereof. The products of each step in the preparations and examples below can be recovered by conventional methods well known in the art, including extraction, evaporation, precipitation, chromatography, filtration, trituration, and crystallization. The reagents and starting materials are readily available to one of ordinary skill in the art.

In an optional step, a pharmaceutically acceptable salt of a compound of Formula I, such as a hydrochloride salt, can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The following preparations and examples further illustrate the invention.

Preparation 1

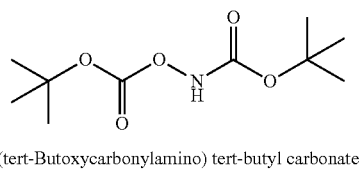

(tert-Butoxycarbonylamino) tert-butyl carbonate

A mixture of hydroxylamine hydrochloride (550.0 g, 7.9 mol), water (5.5 L) and a solution of heptane/MTBE (5:1, 5.5 L) is cooled to −5° C. A pre-cooled (−5° C.) solution of di-t-butyldicarbonate (3.55 Kg, 16.3 mol), triethylamine (1.67 Kg, 16.5 mol) as a solution in heptane/MTBE (5:1, 1.1 L) is slowly added over 2 hours. The reaction is stirred at −5° C. for 1 hour and is then warmed to room temperature and stirred overnight. The layers are separated and the organic layer is washed twice with saturated aqueous ammonium chloride (2 L) and saturated aqueous sodium chloride solution (1 L), dried over sodium sulphate, filtered, and concentrated to give an oil which crystallizes to a white solid. The solid is stirred with heptane (1 L) in an ice-water bath and filtered to give the title product (1360.2 g, 73%). $^1$H NMR (d$_6$-DMSO) δ 10.83-10.58 (m, 1H), 1.43 (d, J=11.3 Hz, 18H).

Preparation 2

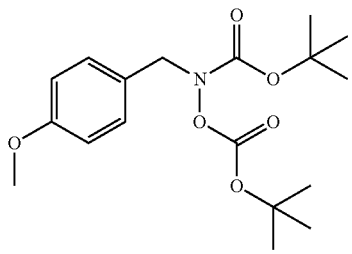

[tert-Butoxycarbonyl-[(4-methoxyphenyl)methyl]amino] tert-butyl carbonate

A 20 L reactor, under nitrogen is charged with (tert-butoxycarbonylamino) tert-butyl carbonate (812.9 g, 3.48 mol), dimethylformamide (4.4 L), potassium carbonate (626.5 g, 4.52 mol) and 1-(chloromethyl)-4-methoxy-benzene (462 mL, 2.56 mol). The mixture is stirred at 40° C. overnight. $^1$H NMR analysis shows incomplete reaction. Additional potassium carbonate (626.5 g, 4.52 mol) is added and the mixture is stirred at 40° C. $^1$H NMR analysis after 48 hours shows the reaction is still incomplete. Additional potassium carbonate (482 g, 3.49 mol) is added and the mixture is stirred at 40° C. $^1$H NMR analysis after overnight reaction shows complete reaction with no starting materials remaining. Water (5 L) and MTBE (5 L) are added and the layers are separated. The organic layer is washed with water (3×3 L), dried over sodium sulphate, and concentrated to give the title compound (1.21 Kg, 98%). $^1$H NMR (d$_6$-DMSO) δ 7.20 (d, J=8.3 Hz, 2H), 6.91 (d, J=8.3 Hz, 2H), 3.73 (s, 2H), 3.35 (s, 3H), 1.41 (s, 18H).

Preparation 3

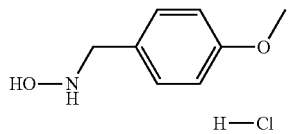

N-[(4-Methoxyphenyl)methyl]hydroxylamine hydrochloride

[tert-Butoxycarbonyl-[(4-methoxyphenyl)methyl]amino] tert-butyl carbonate (1.125 Kg, 3.1 mol) is dissolved in 1,4-dioxane (2.8 L) and a hydrogen chloride solution (4 M in dioxane, 3.15 L, 12.4 mol) is added drop wise over 1 hour 30 minutes. The solution is stirred at room temperature overnight. The title product is collected by filtration as a white solid (488.0 g, 81%). $^1$H NMR (d$_6$-DMSO) δ 11.71 (s, 2H), 10.94 (s, 1H), 7.44 (d, J=8.8 Hz, 2H), 6.95 (d, J=8.8 Hz, 2H), 4.22 (s, 2H), 3.75 (s, 3H).

Preparation 4

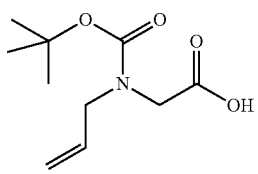

2-(Allyl(tert-butoxycarbonyl)amino)acetic acid

To a round bottom flask containing potassium carbonate (100 g, 724 mmol), sodium iodide (110 g, 727 mmol), dimethylformamide (300 mL), triethylamine (200 mL, 1.44 mol) and 2-propen-1-amine (24 g, 426 mmol) at 0° C. is added drop wise a solution of ethyl 2-bromoacetate (60.2 g, 360 mmol) in dimethylformamide (40 mL). The reaction is warmed to ambient temperature and stirred for 14 hours. The solids are removed by filtration and washed with diethyl ether. Saturated aqueous sodium chloride solution (1 L) is added to the filtrate and the layers are separated. The aqueous layer is extracted with diethyl ether. The organic phases are combined, dried over magnesium sulfate, filtered, and the solvent is removed under reduced pressure to give a residue. To a solution at 0° C. of crude residue in ethanol (500 ml) and triethylamine (40 g, 395 mmol) is added di-t-butyldicarbonate (105 g, 467 mmol) in one portion. The reaction is warmed to room temperature and stirred for 14 hours. The reaction is concentrated under reduced pressure and is diluted with water (200 mL) and saturated aqueous sodium bicarbonate (200 mL) and extracted with diethyl ether. The organic phases are combined, dried over magnesium sulfate, filtered, and concentrated under reduced pressure to give a residue. This residue is taken up in methanol (200 mL) and 2 N sodium hydroxide (500 mL) is added. The resulting solution is stirred for 3 hours at room temperature. The volume is reduced by approximately 200 ml under reduced pressure and the resulting solution acidified to pH 4 using hydrochloric acid (12 N). The resulting pale orange solid is collected by filtration, washed with water, and dried to give the title compound (50 g, 65%). $^1$H NMR (CDCl$_3$) mixture of two rotamers (50:50) δ 1.43, 1.45 (s, 9H), 3.86-3.99 (m, 4H), 5.10-5.20 (m, 2H), 5.71-5.83 (m, 1H).

Preparation 5

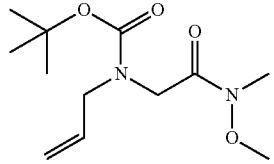

tert-Butyl N-allyl-N-[2-(methoxy(methyl)amino)-2-oxo-ethyl]carbamate 2-(Allyl(tert-butoxycarbonyl)amino)acetic acid (49.6 g, 156 mmol) is added to tetrahydrofuran (600 mL) at 0° C. followed by the addition of triethylamine (36.3 g, 359 mmol) and pivaloyl chloride (31 g, 353 mmol). The reaction is stirred at room temperature for 3 hours and then cooled to 0° C. N,O-dimethylhydroxylamine hydrochloride (28 g, 283 mmol), triethylamine (33 mL, 237 mmol) and tetrahydrofuran (400 mL) are then added. The ice bath is removed and the reaction stirred at room temperature for 3 hours and concentrated under reduced pressure. The resulting solid is dissolved in water and extracted with ethyl acetate. The organic phases are combined, dried over sodium sulfate, filtered, and the solvent removed under reduced pressure to give a residue. The residue is purified by silica gel column chromatography, eluting with 0-50% gradient of acetone in hexanes to give the title compound (32 g, 54%). $^1$H NMR (CDCl$_3$) mixture of two rotamers (60:40) δ 1.42, 1.44 (s, 9H), 3.16, 3.17 (s, 3H), 3.66, 3.69 (s, 3H), 3.88-3.98 (m, 2H), 4.01, 4.11 (s, 2H), 5.10-5.18 (m, 2H), 5.73-5.85 (m, 1H).

Preparation 6

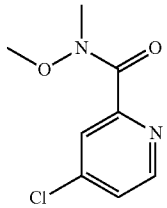

4-Chloro-N-methoxy-N-methyl-pyridine-2-corboxamide

4-Chloropyridine-2-carboxylic acid (40.9 g, 259.59 mmol) is suspended in anhydrous dichloromethane (700 mL) with stirring and with exclusion of moisture (silica gel drying tube is used). The resulting solution is cooled to 0° C. and N-methylmorpholine (129 mL, 1.17 mol), N,O-dimethylhydroxylamine hydrochloride (35.45 g, 363.43 mmol) are added followed by portion wise addition of 1-(3-dimethylaminopropyl)-3-ethylcarbodiimide hydrochloride (69.67 g, 363.43 mmol). After this addition is complete, the reaction is warmed to room temperature and stirred at that temperature overnight. Water (600 mL) is added and the layers are separated. The aqueous layer is re-extracted twice with dichloromethane (300 mL). The organic layers are combined, washed with brine (400 mL) and dried over anhydrous sodium sulphate. The solvent is removed under reduced pressure to give a dark oil. This is purified by silica gel column chromatography using a gradient of 0 to 50% ethyl acetate in iso hexane to give the title compound (23.7 g, 46%). ES/MS (m/e) 201/203.

Preparation 7

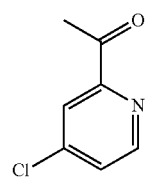

1-(4-Chloropyridin-2-yl)ethanone

Methyl magnesium bromide (3 M in diethyl ether) (59 mL; 177.20 mmol) is added to anhydrous tetrahydrofuran (150 mL) with stirring under nitrogen. The resulting solution is cooled to −15° C. and a solution of 4-chloro-N-methoxy-N-methyl-pyridine-2-carboxamide (23.7 g 1.00 118.13 mmol) in anhydrous tetrahydrofuran (150 mL) is added drop wise over 20 minutes keeping the temperature between 0 and −15° C. After this addition is complete the reaction is stirred at 0° C. for 45 minutes. The reaction is then cooled to −15° C. and is slowly quenched by careful drop wise addition of water (250 mL). Saturated aqueous ammonium chloride solution (250 mL) and diethyl ether (200 mL) are added. The layers are separated and the aqueous layer is re-extracted twice with diethyl ether (200 mL). The combined organic extracts are dried over anhydrous sodium sulphate, filtered, and the solvent is removed under reduced pressure to give the title compound as a yellow oil (18.6 g). ES/MS 156/158 (M+1).

Preparation 8

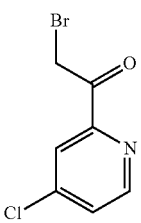

2-Bromo-1-(4-chloro-2-pyridyl)ethanone 1-(4-Chloro-2-pyridyl)ethanone (24.4 g, 156.83 mmol) is dissolved in glacial acetic acid (224 mL) with stirring. A solution of hydrogen bromide (32% in acetic acid) (34 mL) is added followed by slow addition of bromine (8.2 mL, 159.97 mmol). The resulting solution is heated at 75° C. for 3.5 hours and then is immediately cooled in an ice-bath. Saturated aqueous sodium hydrogen carbonate (1 L) is slowly added to the cooled reaction mixture with stirring, followed by solid sodium hydrogen carbonate to adjust the pH of the solution to 7. Ethyl acetate (400 mL) is then added and the layers are separated. The aqueous layer is re-extracted with ethyl acetate (3×400 mL). The organic extracts are combined, dried over anhydrous sodium sulphate, filtered, and concentrated under reduced pressure to give a brown crystalline solid. The isolated solid is triturated with isohexane and is further dried under vacuum to give the title compound (21 g). The product remaining in the isohexane is recovered by silica gel column chromatography using a 0 to 40% dichloromethane in isohexane gradient to give an additional 5.5 g of title product which gives a combined yield (26.5 g, 72%). ES/MS (m/e) 234/236/238 (M+1).

Preparation 9

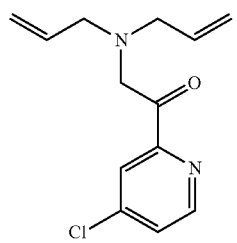

1-(4-Chloro-2-pyridyl)-2-(diallylamino)ethanone

N-Allylprop-2-en-1-amine (15.8 g, 158.2 mmol) is dissolved in anhydrous tetrahydrofuran (283 mL) under nitrogen with stirring. Triethylamine (79 mL) is added and the resulting solution is cooled down to 0° C. A solution of 2-bromo-1-(4-chloro-2-pyridyl)ethanone (26.5 g, 113.0 mmol) in anhydrous tetrahydrofuran (126 mL) is added drop wise (during this addition the color of the reaction changed from colorless to yellow, to orange and then finally to red). After 1.5 hours, water (500 mL) is added and the solvent is removed under reduced pressure. The resulting aqueous solution is extracted with ethyl acetate (5×250 mL). To the combined organic extracts is added anhydrous sodium sulphate. The resulting suspension is filtered through a thin pad of silica gel and diatomaceous earth. The pad is washed with ethyl acetate (1 L). The filtrate is then concentrated under reduced pressure to give the title compound (23.6 g). ES/MS (m/e) 251/253 (M+1). This intermediate has limited stability, is not stored, and is used directly without further purification.

Preparation 10

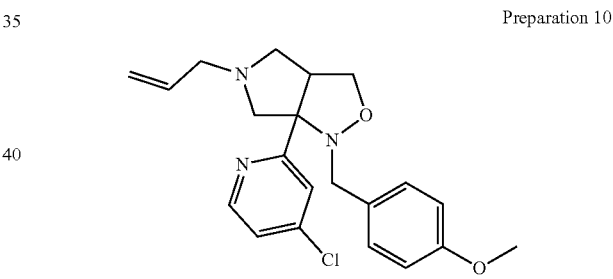

5-Allyl-6a-(4-chloro-2-pyridyl)-1-[(4-methoxyphenyl)methyl]-3,3a,4,6-tetrahydropyrrolo[3,4-c]isoxazole 1-(4-Chloro-2-pyridyl)-2-(diallylamino)ethanone (23.6 g, 94.4 mmol) is dissolved in anhydrous toluene (343 mL) with stirring under nitrogen. N-[(4-Methoxyphenyl)methyl] hydroxyl amine hydrochloride (27.9 g, 146.9 mmol), triethylamine (23.6 mL, 169.5 mmol), and titanium (IV) ethoxide (35.4 mL, 38.7 g, 169.5 mmol) are added sequentially. The resulting reaction mixture is heated at 70° C. under nitrogen. After 8 hours the reaction is cooled and stirred at room temperature over a weekend. Diethyl ether (1 l) and water (500 mL) are then added. The precipitated solid is filtered off through a diatomaceous earth pad. The pad is washed thoroughly with diethyl ether (500 mL). The phases are separated and the aqueous phase is re-extracted with diethyl ether (300 mL). The combined organic phases are dried over anhydrous sodium sulphate and filtered to give a brown oil. This is purified by silica gel column chromatography using a 0 to 20% gradient of tetrahydrofuran in chloroform to give the title compound as a pale brown oil (17.5 g, 40%). ES/MS (m/e) 386/388

Preparation 11

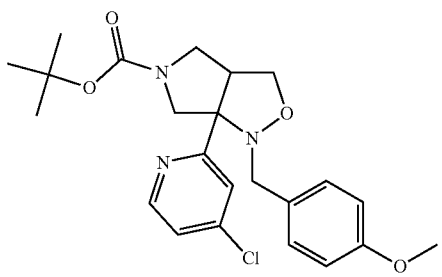

tert-Butyl 6a-(4-chloro-2-pyridyl)-1-[(4-methoxyphenyl)methyl]-3,3a,4,6-tetrahydropyrrolo[3,4-c]isoxazole-5-carboxylate 5-Allyl-6a-(4-chloro-2-pyridyl)-1-[(4-methoxyphenyl)methyl]-3,3a,4,6-tetrahydropyrrolo[3,4-c]isoxazole (17.5 g, 45.35 mmol) is dissolved in anhydrous dichloromethane (230 mL) with stirring under nitrogen. N,N-Dimethylbarbituric acid (38.24 g, 244.89 mmol) and tetrakis(triphenylphosphine)palladium (5.24 g, 4.53 mmol) are added under a stream of nitrogen and nitrogen is bubbled through the solution for several minutes. The resulting solution is then heated at 30° C. under nitrogen for 2 hours. The reaction is then cooled to room temperature. Di-t-butyldicarbonate (10.10 g, 46.26 mmol) and triethylamine (7 mL, 52.15 mmol) are added and the resulting solution is stirred at room temperature for 2 hours. The reaction mixture is concentrated under reduced pressure to give an amber colored semi-solid which is then re-dissolved in ethyl acetate (500 mL). The resulting solution is washed with saturated aqueous sodium bicarbonate solution (2×250 mL). The organic phase is dried over anhydrous sodium sulphate, filtered, and concentrated under reduced pressure to give a dark oil. The oil is purified by silica gel column chromatography using a 0 to 70% ethyl acetate in isohexane gradient to give the title compound as a yellow foam (14.8 g, 73%). ES/MS (m/e) 446 (M+1).

Preparation 12

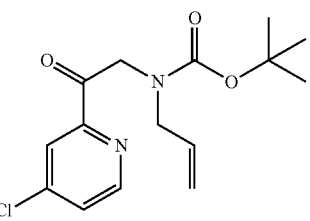

tert-Butyl N-allyl-N-[2-(4-chloro-2-pyridyl)-2-oxo-ethyl]carbamate

To a stirred solution of tetrahydrofuran (60 mL) under nitrogen at −10° C. (methanol-ice bath) is added isopropylmagnesium chloride lithium chloride complex solution (56.84 mL, 73.89 mmol, 1.3 M in tetrahydrofuran). A solution of 2-bromo-4-chloro-pyridine (9.48 g, 49.26 mmol) in tetrahydrofuran (60 mL) is added drop wise ensuring the temperature did not rise above 0° C. during the addition. After 40 minutes the solution is a clear light orange color and tert-butyl N-allyl-N-[2-(methoxy(methyl)amino)-2-oxo-ethyl]carbamate (19.09 g, 73.89 mmol) in tetrahydrofuran (27 mL) is added again ensuring the temperature does rise above 0° C. After the addition is complete, the resulting brown colored solution is then allowed to warm to room temperature. After 2 hours the reaction is quenched by the addition of saturated aqueous ammonium chloride solution followed by a small volume of water. Ethyl acetate is added and the layers are separated. The aqueous layer is re-extracted with ethyl acetate (4×). The organic layers are combined, dried over anhydrous magnesium sulfate, filtered, and concentrated to give a brown oil. The crude product is purified by silica gel column chromatography using a 0 to 30% ethyl acetate in isohexane gradient to give the title compound as a clear pale yellow oil (10.1 g, 66%). ES/MS (m/e) 333 (M+23).

Preparation 13

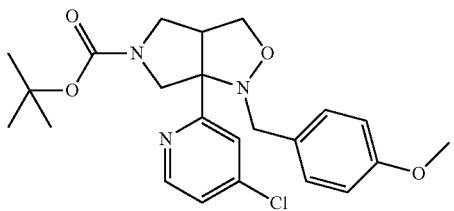

tert-Butyl 6a-(4-chloro-2-pyridyl)-1-[(4-methoxyphenyl)methyl]-3,3a,4,6-tetrahydropyrrolo[3,4-c]isoxazole-5-carboxylate To a stirred solution of tert-butyl N-allyl-N-[2-(4-chloro-2-pyridyl)-2-oxo-ethyl]carbamate (10.10 g, 32.50 mmol) in toluene (230 mL) under nitrogen is added N-[(4-methoxyphenyl)methyl]hydroxylamine hydrochloride (6.47 g, 34.12 mmol), triethylamine (4.76 mL, 34.12 mmol) and titanium (IV) ethoxide (14.27 mL, 68.25 mmol). The resulting solution is warmed to 70° C. under nitrogen. After 3.5 hours the reaction is cooled to room temperature. Water and ethyl acetate are added and the resulting suspension is filtered through diatomaceous earth. The pad of diatomaceous earth is washed well with ethyl acetate. The phases are separated and the organic phase is washed with brine, dried over anhydrous magnesium sulfate, filtered, and concentrated to give an orange oil. The oil is purified by silica gel column chromatography using a 0 to 25% ethyl acetate in isohexane gradient to give the title compound (11.72 g; 81%) as a clear yellow oil. ES/MS (m/e) 446 (M+1).

Preparation 14

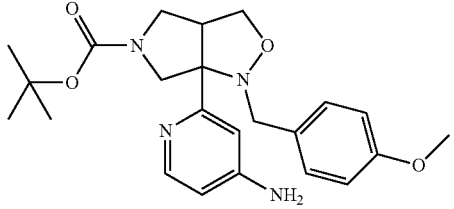

tert-Butyl 6a-(4-amino-2-pyridyl)-1-[(4-methoxyphenyl)methyl]-3,3a,4,6-tetrahydropyrrolo[3,4-c]isoxazole-5-carboxylate tert-Butyl 6a-(4-chloro-2-pyridyl)-1-[(4-methoxyphenyl)methyl]-3,3a,4,6-tetrahydropyrrolo[3,4-c]isoxazole-5-carboxylate (9.4 g, 21.1 mmol), JohnPhos (2.0 g, 6.3 mmol), tris(dibenzylideneacetone)dipalladium (0) (3.0 g, 3.2 mmol), benzophenone imine (7.4 mL, 42.3 mmol), and sodium t-butoxide (6.1 g, 63.4 mmol) are added together in toluene (121 mL). The resulting mixture is thoroughly degassed by freezing with liquid nitrogen under an atmosphere of nitrogen gas and subsequent melting under vacuum in a water bath to room temperature. This procedure is repeated 4 times. The reaction is then heated at 75° C. with stirring under nitrogen for 1.5 hours. The reaction is cooled to room temperature and is diluted with ethyl acetate. The resulting suspension is filtered through a pad of diatomaceous earth and the pad is washed well with ethyl acetate. The solvents are evaporated to give the intermediate imine. This is re-dissolved in methanol (235 mL) and sodium acetate (7.0 g, 84.6 mmol) and hydroxylamine hydrochloride (5.9 g, 84.6 mmol) are added. The resulting mixture is then stirred at room temperature for 1.5 hours. The reaction is quenched with aqueous sodium hydrogen carbonate and the methanol is removed under reduced pressure. The remaining aqueous layer is then extracted with ethyl acetate (2×). The combined organic layers are washed with brine, dried over anhydrous magnesium sulfate, filtered, and concentrated under reduced pressure to give an orange oil. The crude product is purified by silica gel column chromatography using a gradient of 0 to 10% 2 M ammonia in methanol solution in dichloromethane to give the title compound as a brown gum and mixed product containing fractions. The mixed fractions are combined and further purified in two lots using silica gel column chromatography using a gradient of 0 to 5% 2 M ammonia in methanol solution in dichloromethane to give additional product to give a combined yield of the title compound (6.72 g, 75%) as a light brown solid. ES/MS (m/e) 427 (M+1).

Preparation 15

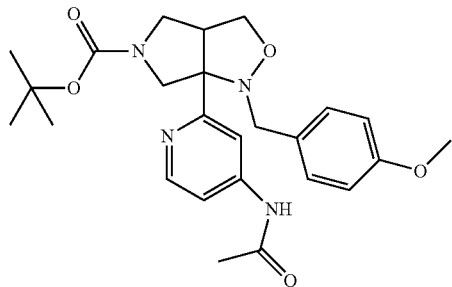

tert-Butyl 6a-(4-acetamido-2-pyridyl)-1-[(4-methoxyphenyl)methyl]-3,3a,4,6-tetrahydropyrrolo[3,4-c]isoxazole-5-carboxylate tert-Butyl 6a-(4-amino-2-pyridyl)-1-[(4-methoxyphenyl)methyl]-3,3a,4,6-tetrahydropyrrolo[3,4-c]isoxazole-5-carboxylate (3.06 g, 7.17 mmol) is placed in a 250 mL flask and ethyl acetate (16 mL) is added with stirring under nitrogen. To the resulting suspension is added 1-propanephosphonic acid cyclic anhydride (≥50 wt % in ethyl acetate) (11 mL, 17.92 mmol), triethylamine (3.50 mL, 25.09 mmol) and acetic acid (616 µL, 10.75 mmol). The resulting solution is heated at 75° C. under nitrogen. After 1 hour the reaction is cooled to room temperature. Ethyl acetate and saturated aqueous sodium hydrogen carbonate solution are added. The layers are separated and the aqueous phase is re-extracted with ethyl acetate (2×). The combined organic layers are dried over anhydrous magnesium sulfate, filtered, and concentrated to give the title product as an amber colored foam (3.11 g, 92%). ES/MS (m/e) 469 (M+1).

Preparation 16

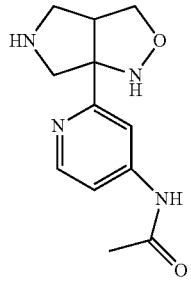

N-[2-(1,3,3a,4,5,6-Hexahydropyrrolo[3,4-c]isoxazol-6a-yl)-4-pyridyl]acetamide tert-Butyl 6a-(4-acetamido-2-pyridyl)-1-[(4-methoxyphenyl)methyl]-3,3a,4,6-tetrahydropyrrolo[3,4-c]isoxazole-5-carboxylate (3.11 g, 6.64 mmol) is taken up in trifluoroacetic acid (10 mL) with stirring and the resulting solution is heated at 50° C. After 1.5 hours the reaction is cooled and concentrated under reduced pressure. The resulting dark oil is re-dissolved in dichloromethane/methanol solution and is loaded onto two ion exchange columns (25 g). The material is eluted with methanol then 2 M ammonia in methanol solution. The basic fraction is concentrated under reduced pressure to give a thick brown oil (1.71 g, 88%). ES/MS (m/e) 248 (M+1).

Preparation 17

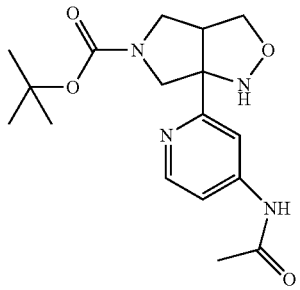

tert-Butyl 6a-(4-acetamido-2-pyridyl)-3,3a,4,6-tetrahydro-1H-pyrrolo[3,4-c]isoxazole-5-carboxylate N-[2-(1,3,3a,4,5,6-Hexahydropyrrolo[3,4-c]isoxazol-6a-yl)-4-pyridyl]acetamide (1.71 g, 5.85 mmol) is dissolved in dichloromethane (anhydrous) (13 mL) with stirring and di-t-butyldicarbonate (1.28 g, 5.86 mmol) is added followed by triethylamine (810 µL, 5.81 mmol). The resulting solution is stirred at room temperature for 1 hour and 45 minutes. The reaction is diluted with dichloromethane and is washed with brine. The organic layer is dried over anhydrous magnesium sulfate, filtered, and evaporated under reduced pressure to give the title product as a pale yellow foam (2.05 g, quantitive). ES/MS (m/e) 349 (M+1).

Preparation 18

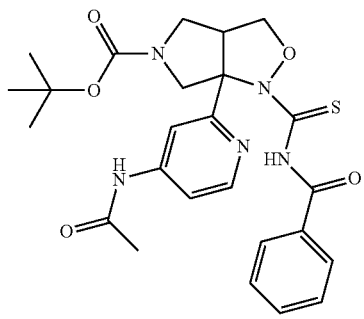

tert-Butyl 6a-(4-acetamido-2-pyridyl)-1-
(benzoylcarbamothioyl)-3,3a,4,6-
tetrahydropyrrolo[3,4-c]isoxazole-5-carboxylate tert-Butyl 6a-(4-acetamido-2-pyridyl)-3,3a,4,6-tetrahydro-1H-pyrrolo[3,4-c]isoxazole-5-carboxylate (2.05 g, 5.88 mmol) is taken up in anhydrous tetrahydrofuran (15.0 mL) with stirring under nitrogen. Benzoyl isothiocyanate (900 µL, 6.54 mmol) is added and the reaction is stirred at room temperature under nitrogen. After 2 hours the reaction is concentrated under reduced pressure to give a pale yellow oil. The oil is purified by silica gel column chromatography using a gradient of 20 to 100% ethyl acetate in cyclohexane to give the title product as a cream colored foam (2.14 g, 66%). ES/MS (m/e) 512 (M+1).

Preparation 19

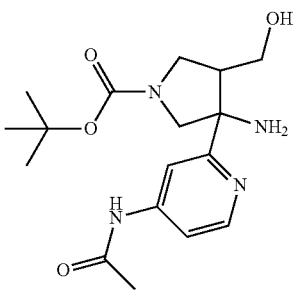

tert-Butyl 3-(4-acetamido-2-pyridyl)-3-
(benzoylcarbamothioylamino)-4-
(hydroxymethyl)pyrrolidine-1-carboxylate tert-Butyl 6a-(4-acetamido-2-pyridyl)-1-(benzoylcarbamothioyl)-3,3a,4,6-tetrahydropyrrolo[3,4-c]isoxazole-5-carboxylate (2.14 g, 3.86 mmol) is dissolved in ethanol (40 mL) and is placed in a large Parr hydrogenation bottle. Palladium hydroxide (20 wt % on carbon, 877 mg) is added under a nitrogen atmosphere and it is then placed on a Parr hydrogenation apparatus and hydrogenated at 50 psi for 24 hours. The reaction suspension is diluted with ethanol and filtered through diatomaceous earth. The pad is washed with ethyl acetate. The combined filtrates are concentrated under reduced pressure to give the title product (2.03 g, 96%) which is used without further purification. ES/MS (m/e) 514 (M+1).

Alternate Preparation 19 tert-Butyl 3-(4-acetamido-2-pyridyl)-3-amino-4-(hydroxymethyl)pyrrolidine-1-carboxylate (1.43 g, 4.08 mmol) is dissolved in anhydrous tetrahydrofuran (27 mL). Benzoyl isothiocyanate (578.49 µL, 4.20 mmol) is added and the resulting mixture is stirred at room temperature for 2 hours under nitrogen. The solvent is then removed under reduced pressure to give a yellow solid foam. This material is purified by silica gel column chromatography using a 0 to 100% ethyl acetate in cyclohexane gradient to give the title compound as a white solid (2.1 g, quantitative). ES/MS (m/e) 514 (M+1).

Preparation 20 tert-Butyl 3-(4-acetamido-2-pyridyl)-3-
amino-4-(hydroxymethyl)pyrrolidine-1-
carboxylate Tert-Butyl 6a-(4-acetamido-2-pyridyl)-3,3a,4,6-tetrahydro-1H-pyrrolo[3,4-c]isoxazole-5-carboxylate (2.026 g, 5.82 mmol) is dissolved in ethanol (145 mL) with sonication. The resulting solution is cycled twice through a palladium hydroxide (20 wt % supported on carbon midi cartridge at 70° C. at 3 ml/min on a flow hydrogenator operating at 85 bar pressure and 100% hydrogen production. Ethanol is removed under reduced pressure to give the title compound as a white foam (1.98 g) with low level impurities present which is used without further purification. ES/MA (m/e) 351 (M+1).

Preparation 21

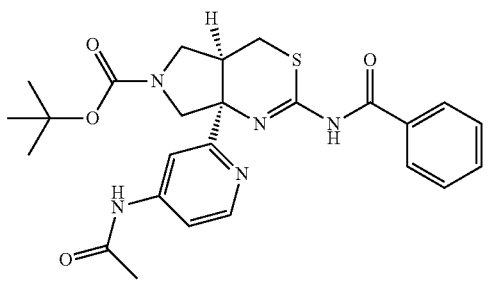

Racemic (cis)-tert-Butyl 7a-(4-acetamido-2-pyridyl)-2-
benzamido-4,4a,5,7-
tetrahydropyrrolo[3,4-d][1,3]thiazine-6-carboxylate To a stirred solution of tert-butyl 3-(4-acetamido-2-pyridyl)-3-(benzoylcarbamothioylamino)-4-(hydroxymethyl)pyrrolidine-1-carboxylate (5.16 g, 8.53 mmol) in tetrahydrofuran (80 mL) is added 1,1'-carbonyldiimidazole (1.84 g, 11.35 mmol) under nitrogen. The resulting solution is stirred at room temperature. After 4 hours, additional 1,1'-carbonyldiimidazole (968.52 mg, 5.97 mmol) is added and the reaction is continued at room temperature. After a further 3.5 hours the intermediate imidazole adduct has been formed completely, ES/MS 608 (M+1). The reaction is then warmed to 75° C., moisture is excluded using a silica gel drying tube, and the mixture is stirred overnight. The reaction is cooled to room temperature and diluted with ethyl acetate. The resulting solution is washed with water, dried over anhydrous magnesium sulfate, filtered and concentrated under reduced pressure to give a yellow oil. The residue is purified by silica gel column chromatography using a gradient of 0 to 100% ethyl acetate in isohexane to give the title compound (3.31 g; 78%) as a light yellow solid. ES/MS (m/e) 496 (M+1).

azin-2-yl]benzamide (2.90 g, 6.61 mmol) in 1,4-dioxane (100 mL) is added 5-fluoro-2-chloropyrimidine (3.15 mL, 33.03 mmol) and diisopropylethylamine (5.8 mL, 33.03 mmol). The resulting solution is stirred at 100° C. for 18 hours with exclusion of moisture. The solvent is removed under reduced pressure to give a brown oil. The residue is purified by silica gel column chromatography using a gradient of 0 to 100% ethyl acetate in isohexane to give the title compound (2.60 g; 80%) as a yellow solid. ES/MS (m/e) 492 (M+1).

Preparation 22

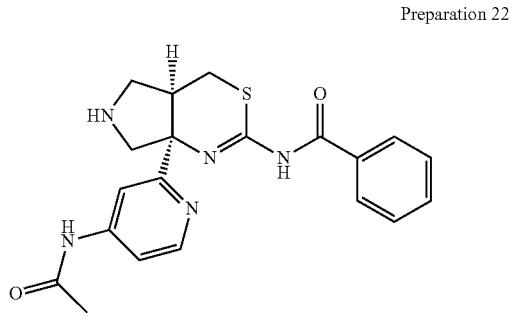

Racemic (cis)-N-[7a-(4-Acetamido-2-pyridyl)-4a,5,6,7-
tetrahydro-4H-pyrrolo[3,4-d][1,3]thiazin-2-yl]benzamide Racemic (cis)-tert-butyl 7a-(4-acetamido-2-pyridyl)-2-benzamido-4a,5,7-tetrahydropyrrolo[3,4-d][1,3]thiazine-6-carboxylate (3.31 g, 6.67 mmol) is suspended in dichloromethane (19 mL) with stirring. Trifluoroacetic acid (9.5 mL) is added to give a clear solution. The solution is stirred at room temperature for 2 hours and the solvent is removed under reduced pressure. The resulting residue is re-dissolved in methanol and this solution is loaded onto an ion exchange column (50 g). The column is eluted with methanol (3 column volumes) then with 2 M ammonia in methanol solution (3 column volumes). The basic washes are combined and concentrated under reduced pressure to give the title compound (2.90 g, quantitative) as a yellow solid. ES/MS (m/e) 396 (M+1).

Preparation 24

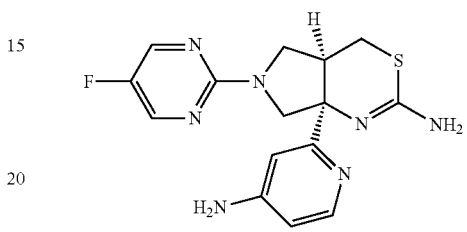

Racemic (cis)-7a-(4-Amino-2-pyridyl)-6-
(5-fluoropyrimidin-2-yl)-4,4a,5,7-
tetrahydropyrrolo[3,4-d][1,3]thiazin-2-amine To a solution of racemic (cis)-N-[7a-(4-acetamido-2-pyridyl)-6-(5-fluoropyrimidin-2-yl)-4,4a,5,7-tetrahydropyrrolo[3,4-d][1,3]thiazin-2-yl]benzamide (2.6 g, 5.3 mmol) in methanol (106 mL) is added lithium hydroxide (1.3 g, 52.8 mmol). The reaction is heated at 70° C. for 8 hours and then at room temperature for the rest of the night. A white solid precipitated out during this time and is collected by filtration. The filtered solid is washed with a small amount of methanol and dried to give the title compound (1.1 g; 59%). ES/MS 346 (M+1). The product remaining in the filtrate is recovered using ion exchange chromatography. The methanol filtrate is loaded directly onto the ion exchange column (50 g) and eluted with methanol (3 column volumes) followed by 2 M ammonia in methanol solution (3 column volumes). The basic eluant is concentrated under reduced pressure to give an additional 700 mg of the title compound of 70% purity. ES/MS 346 (M+1).

Preparation 23

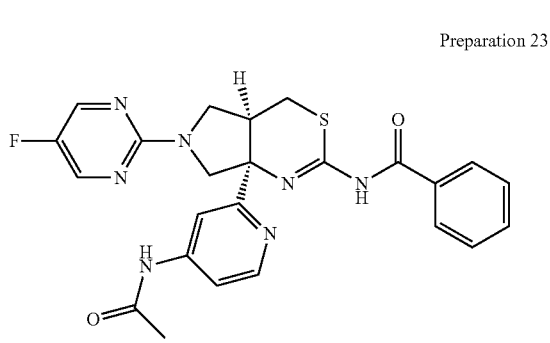

Racemic (cis)-N-[7a-(4-Acetamido-2-pyridyl)-6-
(5-fluoropyrimidin-2-yl)-4,4a,5,7-
tetrahydropyrrolo[3,4-d][1,3]thiazin-2-yl]benzamide To a stirred solution of racemic (cis)-N-[7a-(4-acetamido-2-pyridyl)-4a,5,6,7-tetrahydro-4H-pyrrolo[3,4-d][1,3]thi- Preparation 25

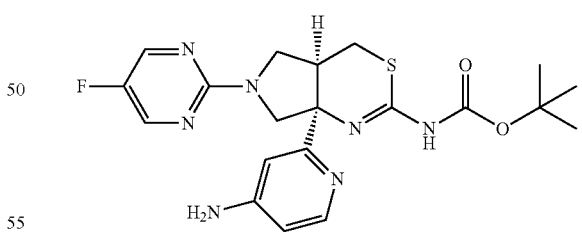

Racemic (cis)-tert-Butyl N-[7a-(4-amino-2-pyridyl)-6-
(5-fluoropyrimidin-2-yl)-4,4a,5,7-
tetrahydropyrrolo[3,4-d][1,3]thiazin-2-yl]carbamate To a stirred suspension of racemic (cis)-7a-(4-amino-2-pyridyl)-6-(5-fluoropyrimidin-2-yl)-4,4a,5,7-tetrahydropyrrolo[3,4-d][1,3]thiazin-2-amine (1.08 g, 3.12 mmol) in dimethylformamide (17 mL) is added di-t-butyldicarbonate (1.16 g, 5.30 mmol) in dichloromethane (9 mL). The suspension is stirred at room temperature over a weekend. The reaction mixture is partitioned between dichloromethane and brine solution. The organic phase is separated and washed with more brine solution. The organic layer is dried over anhydrous magnesium sulfate, filtered and concentrated under reduced pressure to give a yellow oil. The residue is purified by silica gel column chromatography using a 0 to 5% gradient of 2 M ammonia in methanol solution in dichloromethane to give the title compound (racemate, 1.60 g with 20% residual dimethylformamide/dichloromethane) as a clear gum which is used directly without further purification. ES/MS (m/e) 446 (M+1).

Preparation 26

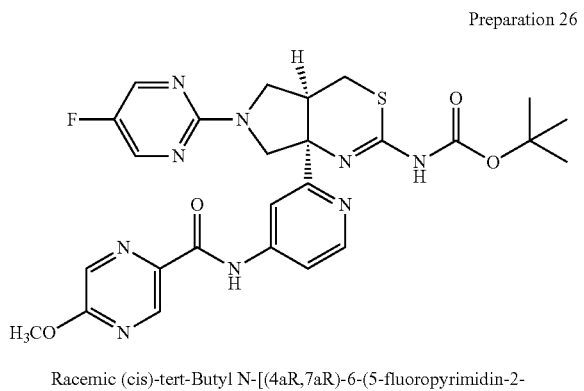

Racemic (cis)-tert-Butyl N-[(4aR,7aR)-6-(5-fluoropyrimidin-2-yl)-7a-[4-[(5-methoxypyrazine-2-carbonyl)amino]-2-pyridyl]-4,4a,5,7-tetrahydropyrrolo[3,4-d][1,3]thiazin-2-yl]carbamate Racemic (cis)-tert-butyl N-[7a-(4-amino-2-pyridyl)-6-(5-fluoropyrimidin-2-yl)-4,4a,5,7-tetrahydropyrrolo[3,4-d][1,3]thiazin-2-yl]carbamate (1.01 g, 2.27 mmol) is dissolved in ethyl acetate (8 mL) with stirring. 1-Propanephosphonic acid cyclic anhydride (≥50 wt % in ethyl acetate solution) (2.31 mL, 3.63 mmol), triethylamine (948 μL, 6.80 mmol) and 5-methoxypyrazine-2-carboxylic acid (454 mg, 2.95 mmol) are then added. The resulting solution is heated at 80° C. under nitrogen for 1 hour 20 minutes and it is then cooled to room temperature. The mixture is diluted with ethyl acetate and saturated aqueous sodium hydrogen carbonate solution and the layers are separated. The aqueous layer is re-extracted with ethyl acetate. The organic layers are combined, dried over anhydrous magnesium sulfate, filtered, and concentrated under reduced pressure to give a brown solid. The residue is purified by silica gel column chromatography using a 0 to 75% gradient of ethyl acetate in isohexane to give the title compound (576 mg, 44%). ES/MS (m/e) 582 (M+1).

Preparation 27

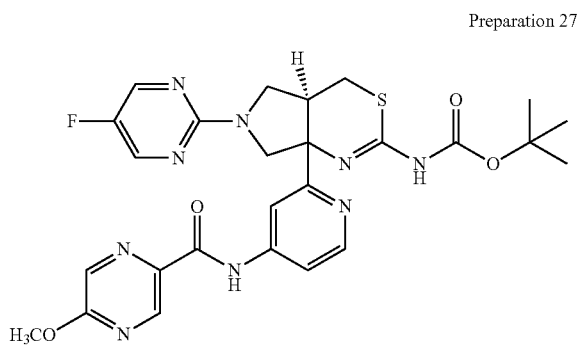

tert-Butyl N-[(4aR,7aR)-6-(5-fluoropyrimidin-2-yl)-7a-[4-[(5-methoxypyrazine-2-carbonyl)amino]-2-pyridyl]-4,4a,5,7-tetrahydropyrrolo[3,4-d][1,3]thiazin-2-yl]carbamate Racemic (cis)-tert-butyl N-[(4aR,7aR)-6-(5-fluoropyrimidin-2-yl)-7a-[4-[(5-methoxy pyrazine-2-carbonyl) amino]-2-pyridyl]-4,4a,5,7-tetrahydropyrrolo[3,4-d][1,3]thiazin-2-yl]carbamate (576 mg, 0.99 mmol) is separated into its constituent enantiomers by chiral SFC (Column: OJ-H, 25 cm×21.2 mm, 5 micron); Mobile Phase: 24% methanol (0.1% ammonia) 76% CO$_2$; Flow: 70 mL/min at UV 220 nm; 35° C.; 12 mg per injection). The second eluting isomer (isomer 2) is the title compound (207 mg, 36%). ES/MS (m/e) 582 (M+1).

EXAMPLE 1

Racemic (cis)-N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide

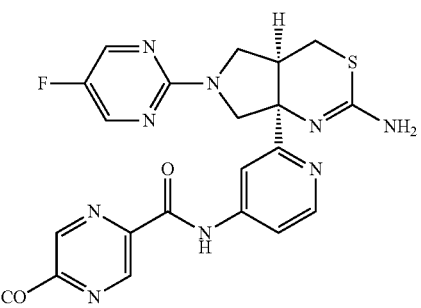

To a solution of racemic (cis)-tert-butyl N-[6-(5-fluoropyrimidin-2-yl)-7a-[4-[(5-methoxypyrazine-2-carbonyl)amino]-2-pyridyl]-4,4a,5,7-tetrahydropyrrolo[3,4-d][1,3]thiazin-2-yl]carbamate (487 mg, 837.30 μmop in dichloromethane (14 mL) is added trifluoroacetic acid (1.7 mL) and the mixture is stirred at room temperature for 1.5 hours. The reaction is diluted with dichloromethane and washed with saturated aqueous sodium hydrogen carbonate. The layers are separated and the aqueous layer is re-extracted with dichloromethane. The organic layers are combined, dried over anhydrous magnesium sulfate, filtered, and concentrated under reduced pressure to give a white solid. The solid is purified by silica gel column chromatography using a 0 to 5% gradient of 2 M ammonia in methanol solution in dichloromethane to give the title compound (126 mg, 31%). ES/MS (m/e) 482 (M+1).

EXAMPLE 2

N-[2-[(4aR,7aR)-2-Amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide

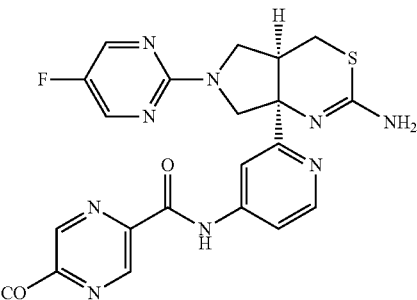

To a solution of tert-butyl N-[(4aR,7aR)-6-(5-fluoropyrimidin-2-yl)-7a-[4-[(5-methoxypyrazine-2-carbonyl)amino]-2-pyridyl]-4,4a,5,7-tetrahydropyrrolo[3,4-d][1,3]thiazin-2-yl]carbamate (isomer 2, 207 mg, 355.90 µmop in dichloromethane (6 mL) is added trifluoroacetic acid (712 µL, 9.41 mmol). The resulting solution is stirred at room temperature for 1.5 hours. The reaction is then diluted with dichloromethane and washed with saturated aqueous sodium hydrogen carbonate solution. The layers are separated and the aqueous layer is re-extracted with dichloromethane. The organic layers are combined, dried over anhydrous magnesium sulfate, filtered, and concentrated under reduced pressure to give a white solid which is dried in a vacuum oven at 35° C. for 5 hours to give the title compound (186 mg, quantitative). ES/MS (m/e) 482 (M+1)

Alternate Preparation of N-[2-[(4aR,7aR)-2-Amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide Racemic (cis)-N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide (126 mg, 0.262 mmol) is separated into its constituent enantiomers by chiral HPLC (Column: AD-H, 25 cm×21.2 mm, 5 micron); Mobile Phase: 1:4 ratio of acetonitrile to methanol (20 mM ammonia in methanol solution); Flow: 30 mL/min at UV variable wavelength detection; 8 mg per injection). The second eluting isomer is the title compound (92 mg, 73%). ES/MS (m/e) 482 (M+1).

EXAMPLE 3

Racemic (cis)-N-[2-[2-Amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide hydrochloride

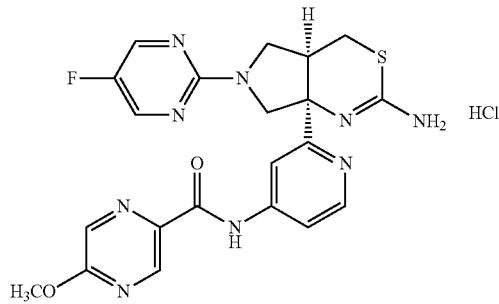 [SMILES: COc1cnc(C(=O)Nc2ccnc([C@]34CN(c5ncc(F)cn5)C[C@H]3CSC(N)=N4)c2)cn1 ; Cl]

Racemic (cis)-N-[2-[2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide (56 mg, 0.116 mmol) is dissolved in acetonitrile (0.35 mL) followed by the addition of 0.1 M aqueous hydrogen chloride solution (1.1 mL). The resulting solution is placed on a freeze drier overnight to give the title compound as a white solid (61 mg, 51%). ES/MS (m/e) 482 (M+1)

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 µM to 0.05 nM in a 96-well round-bottom plate before conducting the in vitro enzymatic and whole cell assays.

In Vitro Protease Inhibition Assays:

Expression of and Purification of huBACE1 Fc Human BACE1 (accession number: AF190725) is cloned from total brain cDNA by RT-PCR. The nucleotide sequences corresponding to amino acid sequences #1 to 460 are inserted into the cDNA encoding human $IgG_1$(Fc) polypeptide (Vassar et al., Science, 286, 735-742 (1999)). This fusion protein of BACE1 (1-460) and human Fc, named huBACE1:Fc, is constructed into the pJB02 vector. Human BACE1 (1-460): Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification. huBACE1:Fc is purified by Protein A chromatography. The enzyme is stored at −80° C. in small aliquots. (See Yang, et. al., J. Neurochemistry, 91(6) 1249-59 (2004).

BACE1 FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., J. Neurochemistry, 91(6) 1249-59 (2004)). The content is mixed well on a plate shaker for 10 minutes. Fifteen µL of two hundred pM human BACE1(1-460):Fc (See Vasser, et al., Science, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $IC_{50}$ values. (See Sinha, et al., Nature, 402, 537-540 (2000) and May, et al., Journal of Neuroscience, 31, 16507-16516 (2011)).

The compound of Example 2 is tested essentially as described above and exhibited an $IC_{50}$ for BACE1 of 0.90 nM (±0.36, n=10) Mean±SEM.

This data demonstrates that the compound of Example 2 inhibits purified recombinant BACE1 enzyme activity in vitro.

Whole Cell Assay for Measuring the Inhibition of Beta-Secretase Activity

PDAPP Primary Neuronal Assay

A confirmatory whole cell assay is also run in primary neuronal cultures generated from PDAPP transgenic embryonic mice (described in Games et al., Nature 373, 523-527 (1995) and May, et al., Journal of Neuroscience, 31, 16507-16516 (2011)). Primary cortical neurons are prepared from Embryonic Day 16 PDAPP embryos and cultured in 96 well plates (15×10$^4$ cells/well in DMEM/F12 (1:1) plus 10% FBS). After 2 days in vitro, culture media is replaced with serum free DMEM/F12 (1:1) containing B27 supplement and 2 µM (final) of Ara-C(Sigma, C1768). At day 5 in vitro, neurons are incubated at 37° C. for 24 hours in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody (for description of antibodies, see Johnson-Wood, et al., *Proc. Natl. Acad. Sci. USA* 94, 1550-1555 (1997)). The concentration of Abeta released in the conditioned media following the compound treatment corresponds to the activity of BACE1 under such conditions. The 10-point inhibition curve is plotted and fitted with the four-parameter logistic equation to obtain $IC_{50}$ values for the Abeta-lowering effect. The compound of Example 2 is tested essentially as described above and exhibits the following activity. $IC_{50}$ for reducing $Abeta_{1-40}$=0.65 nM (±0.11, n=3). $IC_{50}$ for reducing $Abeta_{1-42}$=0.91 nM (±0.16, n=3).

This data demonstrates that the compound of Example 2 inhibits $Abeta_{1-40}$ and $Abeta_{1-42}$ production in whole cells.

I claim:

1. A compound of the formula:

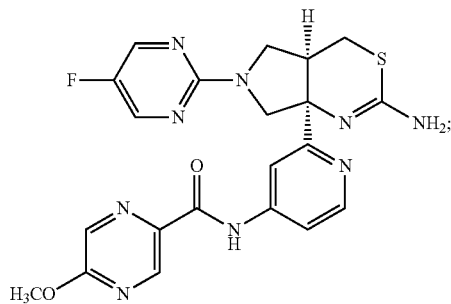

or a pharmaceutically acceptable salt thereof.

2. The compound or salt according to claim 1 which is N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide.

3. The compound according to claim 2 which is N-[2-[(4aR,7aR)-2-amino-6-(5-fluoropyrimidin-2-yl)-4,4a,5,7-tetrahydropyrrolo[3,4-d][1,3]thiazin-7a-yl]-4-pyridyl]-5-methoxy-pyrazine-2-carboxamide.

4. A method of treating Alzheimer's disease, comprising administering to a patient in need of such treatment an effective amount of a compound according to claim 1, or a pharmaceutically acceptable salt thereof.

5. A pharmaceutical composition, comprising a compound or a pharmaceutically acceptable salt thereof according to claim 1 with one or more pharmaceutically acceptable carriers, diluents, or excipients.

6. A method of treating Alzheimer's disease, comprising administering to a patient in need of such treatment an effective amount of a compound according to claim 2, or a pharmaceutically acceptable salt thereof.

7. A pharmaceutical composition, comprising a compound or a pharmaceutically acceptable salt thereof according to claim 2 with one or more pharmaceutically acceptable carriers, diluents, or excipients.

* * * * *